United States Patent
Hori et al.

(10) Patent No.: US 10,556,131 B2
(45) Date of Patent: Feb. 11, 2020

(54) PARTICLE BEAM THERAPY SYSTEM AND METHOD FOR UPDATING PARTICLE BEAM THERAPY SYSTEM

(71) Applicant: Hitachi, Ltd., Tokyo (JP)

(72) Inventors: Yoshihito Hori, Tokyo (JP); Takayoshi Matsushita, Tokyo (JP); Kouji Tobinaga, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/696,521

(22) Filed: Sep. 6, 2017

(65) Prior Publication Data

US 2018/0064957 A1    Mar. 8, 2018

(30) Foreign Application Priority Data

Sep. 8, 2016   (JP) ................. 2016-175173

(51) Int. Cl.
*A61N 5/10* (2006.01)

(52) U.S. Cl.
CPC ......... *A61N 5/1077* (2013.01); *A61N 5/1043* (2013.01); *A61N 5/1075* (2013.01); *A61N 2005/1087* (2013.01)

(58) Field of Classification Search
USPC ...................................................... 250/492.3
See application file for complete search history.

(56) References Cited

U.S. PATENT DOCUMENTS

| 5,349,198 A * | 9/1994 | Takanaka ................. A61N 5/10 250/396 ML |
| 6,683,318 B1 * | 1/2004 | Haberer .................. A61N 5/10 250/492.3 |
| 2011/0220809 A1 | 9/2011 | Yajima et al. |
| 2014/0088336 A1 * | 3/2014 | Hagino ................ A61N 5/1043 600/1 |
| 2014/0296610 A1 | 10/2014 | Nishiuchi |
| 2015/0328483 A1 * | 11/2015 | Odawara ............. A61N 5/1081 600/1 |
| 2016/0074676 A1 | 3/2016 | Yajima et al. |
| 2016/0101298 A1 * | 4/2016 | Otani ...................... H05H 7/04 600/1 |

FOREIGN PATENT DOCUMENTS

| JP | 2011-182987 A | 9/2011 |
| JP | 2013-120483 A | 6/2013 |
| JP | 5409521 B2 | 2/2014 |

OTHER PUBLICATIONS

Japanese Office Action received in corresponding Japanese Application No. 2016-175173 dated Jul. 9, 2019.

* cited by examiner

*Primary Examiner* — Kiet T Nguyen
(74) *Attorney, Agent, or Firm* — Mattingly & Malur, PC

(57) ABSTRACT

A system update method for a particle beam therapy system, includes: a step of providing a new beam transport system in such a manner as to be branched off from an existing beam transport system of the particle beam therapy system; and a step of providing new installation connected to the new beam transport system, in which the branch is provided in a linear section of the existing beam transport system.

14 Claims, 11 Drawing Sheets

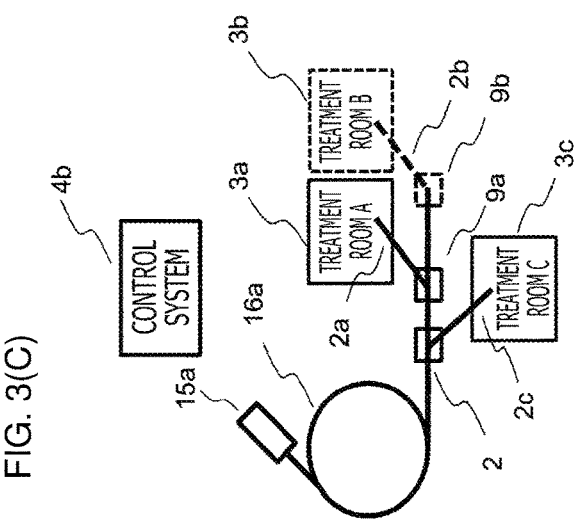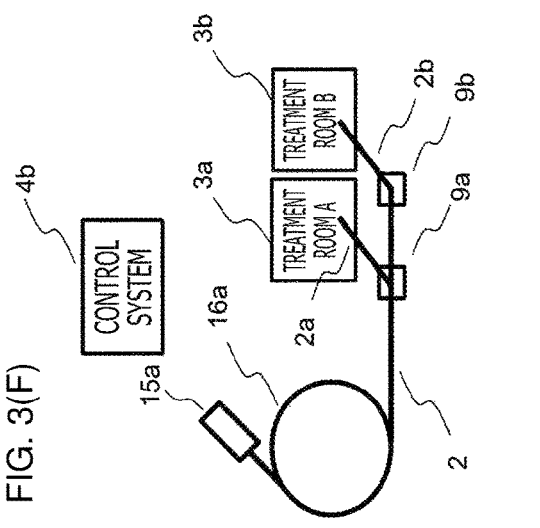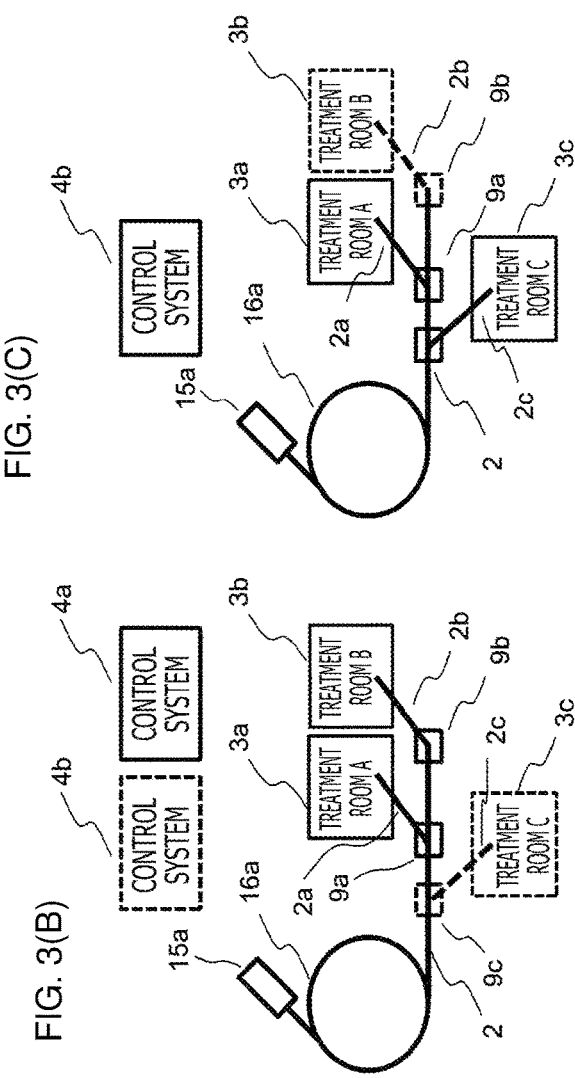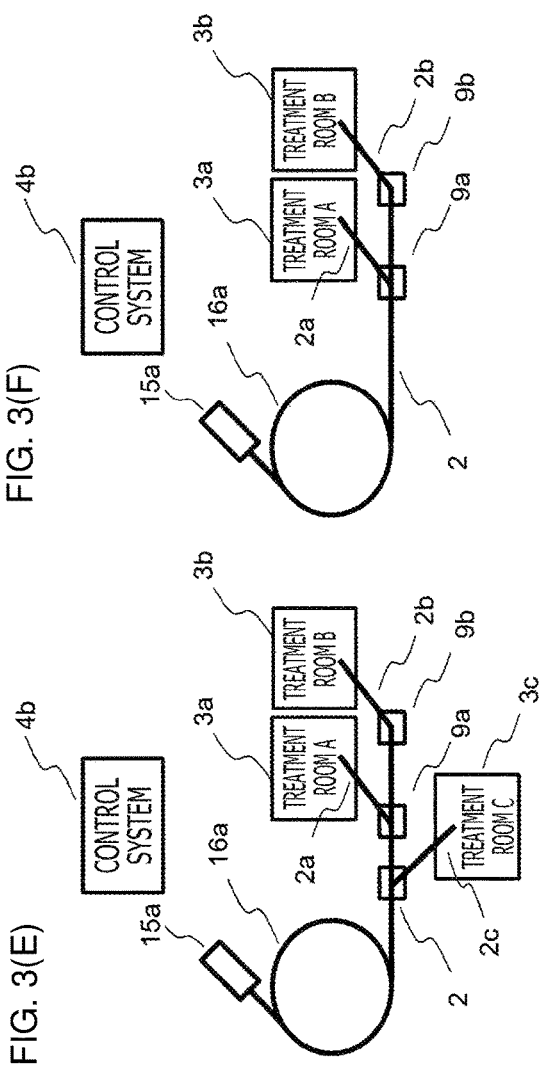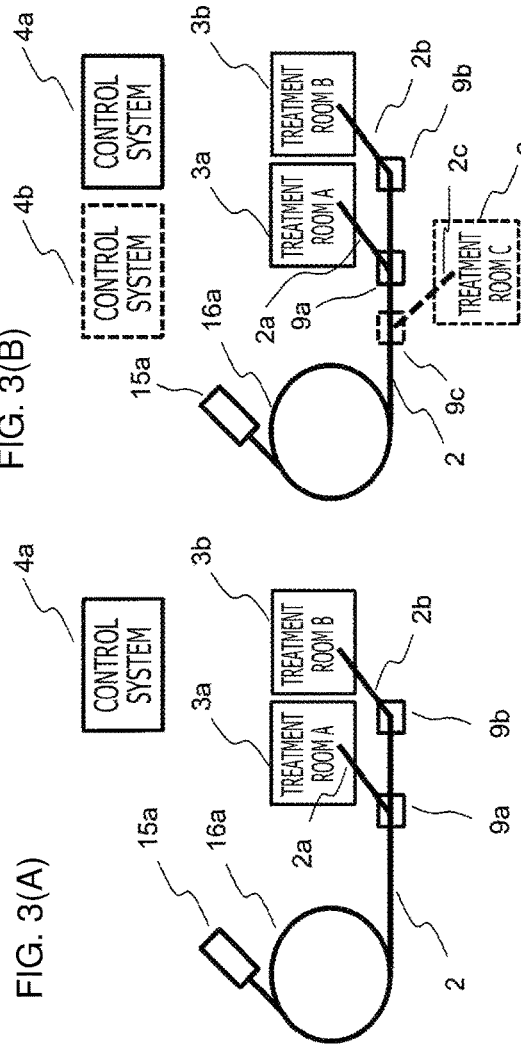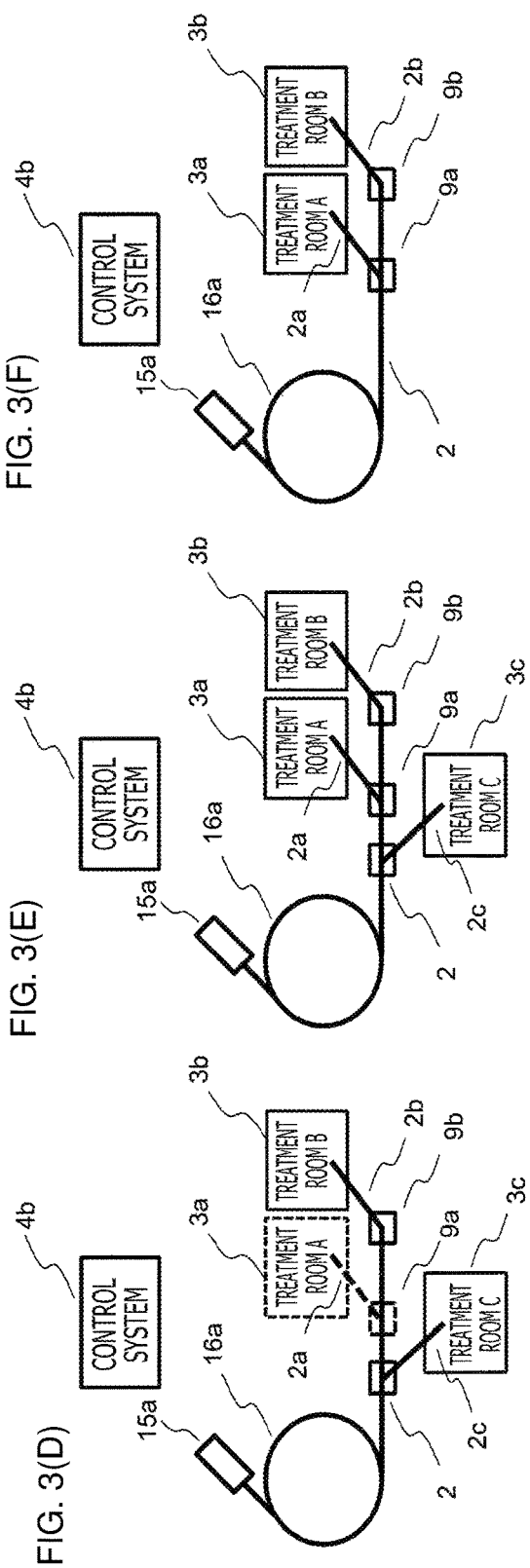

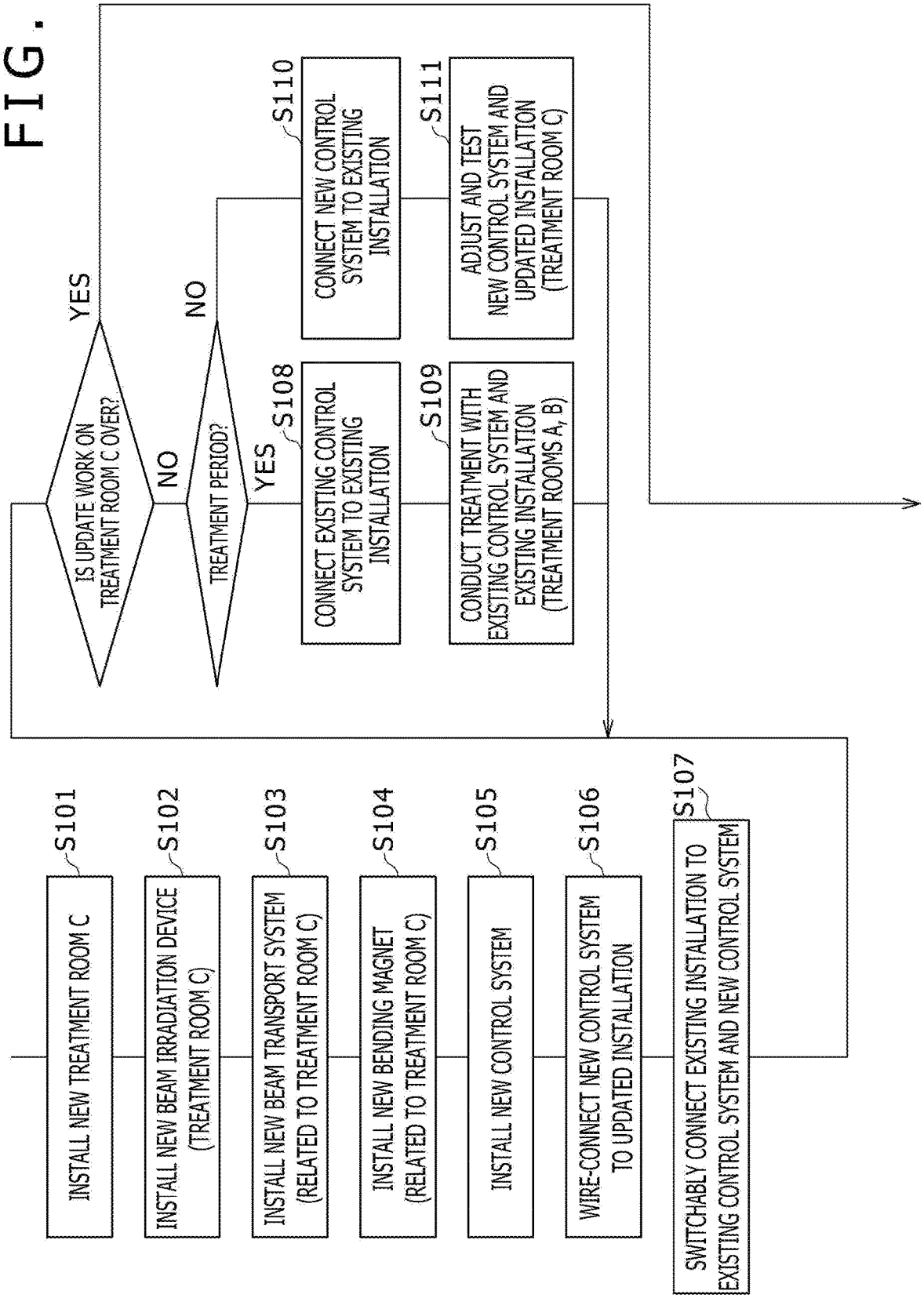

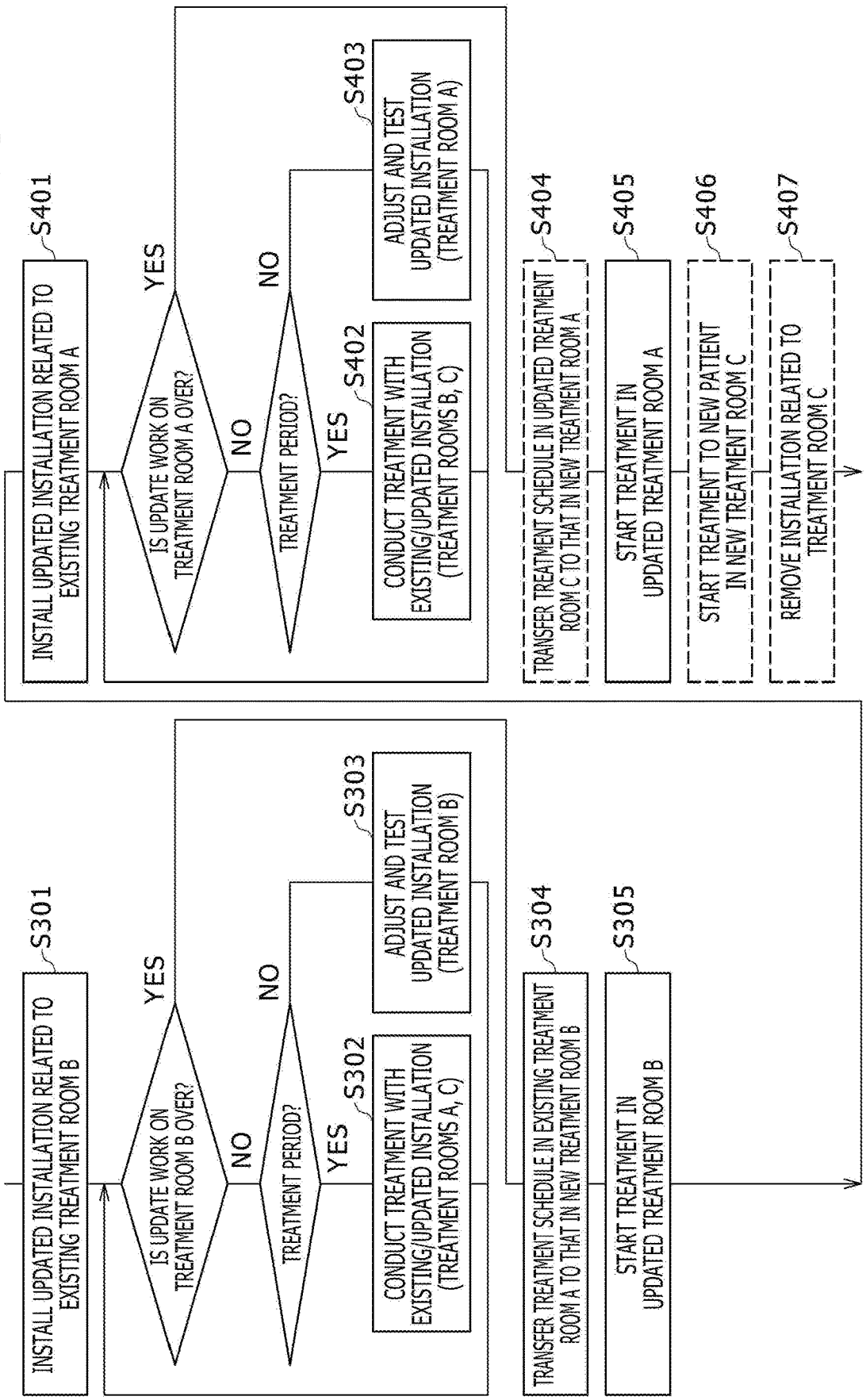

PARTICLE BEAM THERAPY SYSTEM AND METHOD FOR UPDATING PARTICLE BEAM THERAPY SYSTEM

TECHNICAL FIELD

The present invention relates to a particle beam therapy system that makes use of a charged particle beam (an ion beam) of protons, heavy ions or the like, and that is suitable when a new system is introduced or a system is updated while a particle beam treatment is continued.

BACKGROUND ART

There is known a particle beam treatment for irradiating a patient's cancer affected part with an ion beam of protons, heavy ions or the like as a radiation treatment for cancer. A particle beam therapy system needs to make highly accurate beam position adjustment to introduce the ion beam into the affected part, and takes a great deal of time for the adjustment and testing. Patent Documents 1 and 2 describe the adjustment and the testing of the particle beam therapy system.

If the need to update an existing system to a new system in the same site arises due to aging of the existing system, application of improvement following technological advancement, such a flow may be considered as to stop the system, replace the existing system with the new system, and treatment is started with the new system after testing the new system. However, it takes time to adjust and test the system at a time of update and a suspension period of treatment is prolonged. During that period, patients cannot get treatment, it is difficult to maintain installation and maintain employees, and other disadvantages occur. Considering that the system update is accompanied by disadvantages, it is desired to avoid a long suspension period of treatment.

PRIOR ART DOCUMENTS

Patent Documents

Patent Document 1: Japanese Patent No. 5409521
Patent Document 2: US Patent Application Publication No. 2014/0296610

SUMMARY OF THE INVENTION

Problem to be Solved by the Invention

If a full set of the treatment system is replaced for the update, it takes lots of time for the adjustment and testing and the suspension period of treatment is prolonged. As a result, a problem occurs that the number of patients decreases, i.e., patients who could get treatment when the existing system operated cannot get treatment. There are concerns including a decline in sources of revenue as a tradeoff with the maintenance of installation and a shortage of supply of installation relative to demand of patients to be treated. While it is possible to segment a control system, installation, and the like to gradually implement replacement on a part-by-part basis in the case of updating the existing treatment system, the adjustment and testing are inevitable to combinations of existing parts and new parts in consideration of large-scale installation update. As a result, there is no avoiding a shortage of time with handling of the update only at time other than treatment time (for example, during nighttime hours or on holidays) of the existing system. Furthermore, when a problem occurs to the new system after update, the existing system is not quickly available as before even if the new system is returned to the existing system but the adjustment and testing are necessary. Therefore, update work involves a high risk.

An object of the present invention is, therefore, to mitigate the influence of suspension of treatment in an existing system by proposing an update method capable of conducting update work (additional installation, adjustment, and testing of a new system) at time such as nighttime hours or holidays when no treatment is given in the state in which the treatment is maintained in the existing system.

Means for Solving the Problems

To attain the object, the present invention adopts, for example, a configuration according to claims.

While the present invention includes a plurality of means for solving the problems, the following is one example. A system update method for a particle beam therapy system, includes: a step of providing a new beam transport system in such a manner as to be branched off from an existing beam transport system of the particle beam therapy system; and a step of providing new installation connected to the new beam transport system, in which the branch is provided in a linear section of the existing beam transport system.

Effect of the Invention

According to the present invention, it is possible to add a treatment room with a minimum influence on an existing system.

Furthermore, it is possible to update the treatment system in a state in which a particle beam treatment is maintained in an existing system by providing an update method capable of conducting update work (additional installation, adjustment, and testing of a new system) during periods such as nighttime hours or holidays when no treatment is given in the state in which the treatment is maintained in the existing system.

BRIEF DESCRIPTION OF THE DRAWINGS

FIGS. 3(A) to 3(F) are explanatory diagrams of an update procedure related to treatment rooms in the treatment system.

FIG. 10 is an explanatory flowchart 1 of the update procedure related to the treatment rooms in the treatment system.

FIG. 12 is an explanatory flowchart 3 of the update procedure related to the control system in the treatment system.

MODES FOR CARRYING OUT THE INVENTION

Embodiments of the present invention will be described hereinafter with reference to the drawings.

A configuration of a particle beam irradiation system according to the present invention will first be described with reference to FIG. 1.

Figure 1:
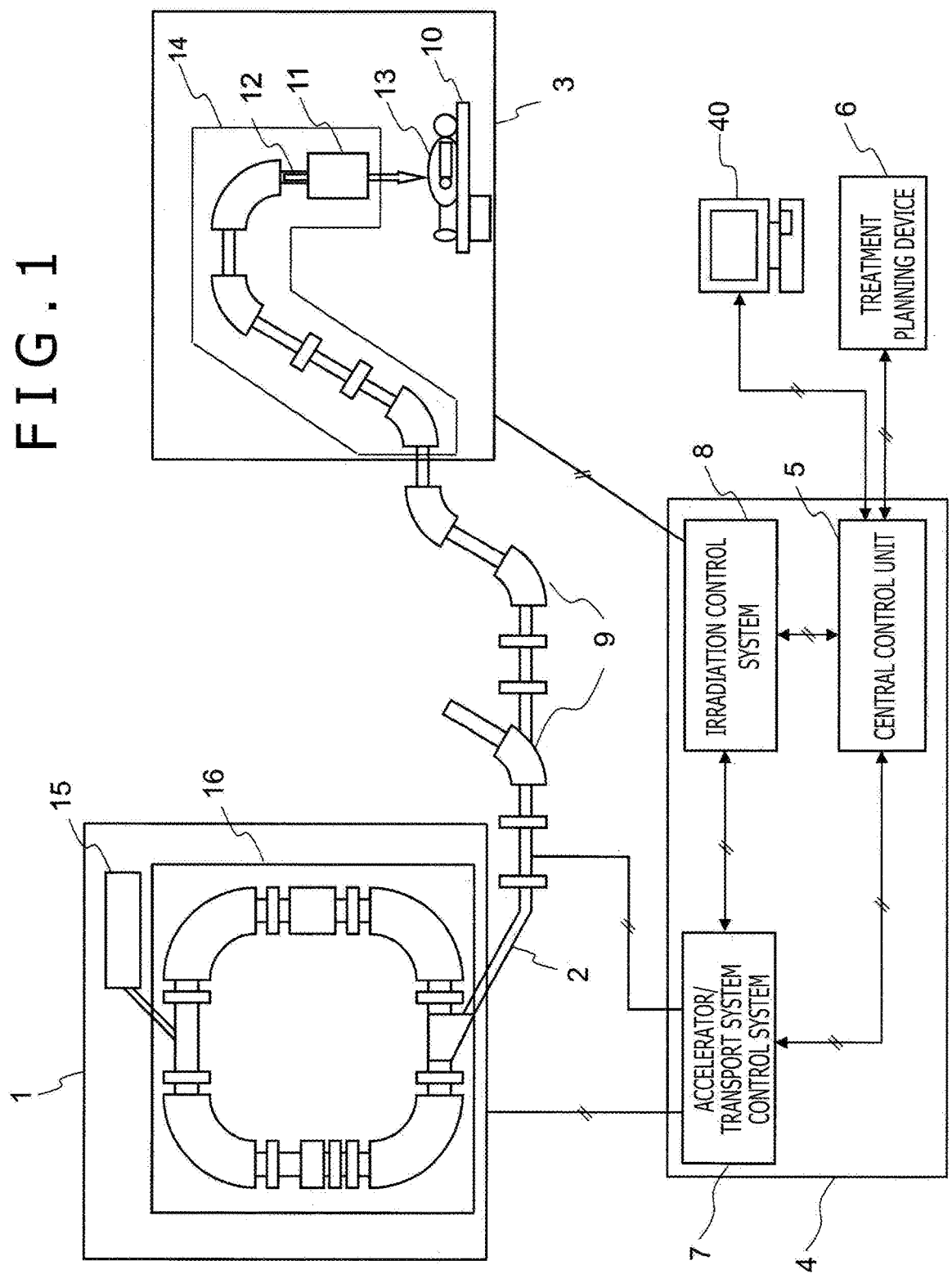
FIG. 1 is a configuration diagram of a particle beam therapy system.

FIG. 1 is a configuration illustrating an overall configuration of the particle beam irradiation system according to a first embodiment of the present invention.

The particle beam irradiation system according to the present embodiment includes a charged particle beam generator 1, a beam transport system 2, a beam irradiation device 3, and a control system 4.

The charged particle beam generator 1 includes an ion source (not shown), a preaccelerator 15, and a circular accelerator (synchrotron) 16. While the synchrotron is taken as the circular accelerator 16 in the present embodiment by way of example, another accelerator such as a cyclotron may be used. The ion source is connected to an upstream side of the preaccelerator 15 and the circular accelerator 16 is connected to a downstream side of the preaccelerator 15.

The beam transport system 2 is connected to a downstream side of the charged particle beam generator 1 and connects the charged particle beam generator 1 to the beam irradiation device 3. A charged particle beam 12 is passed through the beam transport system 2 and guided to the beam irradiation device 3 in each treatment room by bending magnets 9. A plurality of the beam irradiation devices 3 can be provided; in this case, the charged particle beam 12 is guided to the irradiation device that radiates the beam by controlling the corresponding bending magnet 9 out of a plurality of bending magnets 9.

The beam irradiation device 3 is a device for irradiating a patient's affected part with the charged particle beam 12. As shown in FIG. 1, the beam irradiation device 3 generally includes a treatment table 10 on which a patient 13 is placed, an irradiation nozzle (nozzle device) 11, and a rotating gantry 14.

The treatment table 10 is disposed within the treatment room, places thereon the patient 13, and positions the affected part.

An upstream beam monitor, a scanning electromagnet, a dose monitor, and a downstream beam monitor are disposed in the irradiation nozzle 11 along a beam path, and form a radiation field of the beam in the irradiation nozzle 11.

The upstream beam monitor measures a passing position and a beam width (beam diameter) of the charged particle beam 12 incident in the irradiation nozzle 11.

The scanning electromagnet includes a first scanning electromagnet deflecting and scanning the passing charged particle beam in a first direction (for example, an X-axis direction), and a second scanning electromagnet deflecting and scanning the charged particle beam in a second direction (for example, a Y-axis direction) perpendicular to the first direction. Here, the X-axis direction indicates one direction in a plane perpendicular to a travel direction of the charged particle beam incident in the irradiation nozzle 11, while the Y-axis direction indicates a direction perpendicular to the X-axis direction in the plane.

The dose monitor measures an exposure dose of the passing charged particle beam. In other words, the dose monitor is a monitor that monitors an exposure dose of the charged particle beam radiated to the patient.

The downstream beam monitor is installed downstream of the scanning electromagnet and measures the position and the beam width of the passing charged particle beam. In other words, the downstream beam monitor is a monitor that measures the position and the beam width of the charged particle beam scanned by the scanning electromagnet.

The rotating gantry 14 is configured to be rotatable about an isocenter (not shown) and determines an irradiation angle of the beam. By rotation of the rotating gantry 14, the irradiation angle of the charged particle beam 12 radiated to the patient 13 can be changed.

As shown in FIG. 1, the control system 4 includes a central control unit 5, an accelerator/transport system control system 7, and an irradiation control system 8.

The central control unit 5 is connected to a treatment planning device 6, the accelerator/transport system control system 7, the irradiation control system 8, and an operation terminal 40. This central control unit 5 includes a function to calculate a set value of an operation parameter for accelerator operation, an operation parameter for forming the radiation field, a planned beam position and a planned beam width, and a set value of a dose on the basis of set data from the treatment planning device 6. These operation parameters and the monitor set values are output from the central control unit 5 to the accelerator/transport system control system 7 and the irradiation control system 8.

The accelerator/transport system control system 7 is connected to the charged particle beam generator 1 and the beam transport system 2, and controls equipment that constitutes the charged particle beam generator 1 and the beam transport system 2.

The irradiation control system 8 is connected to the beam irradiation device 3 and controls equipment that constitutes the beam irradiation device 3.

The operation terminal 40 includes an input device to which an operator (a health care worker such as a medical doctor or an operator) inputs data and instruction signals, and a display screen.

Figure 2:
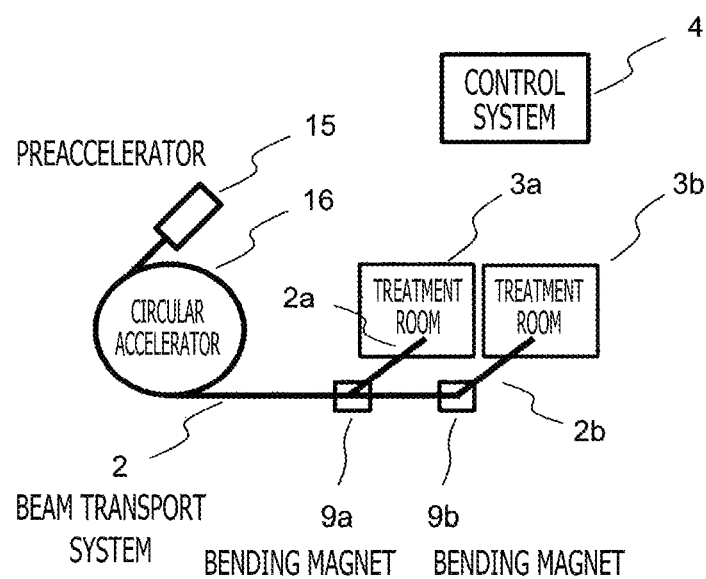
FIG. 2 is a simplified configuration diagram of the particle beam therapy system.

FIG. 2 is a simplified configuration diagram of the particle beam therapy system in a simplified form of FIG. 1. The embodiments will be described hereinafter on the basis of this simplified diagram.

It is noted that the beam irradiation device 3 can be replaced by a fixed irradiation device that does not include the rotating gantry 14.

First Embodiment

In the present embodiment, as shown in FIG. 3(A), a treatment system that includes one circular accelerator 16a and two treatment rooms is assumed as an existing treatment system, and a procedure described below is executed in respect to update of installation related to each treatment room and a control system. It is noted that the treatment system will be described as a typical example since the number of treatment rooms, arrangement, and the like vary with installation. Furthermore, the procedure is illustrated in FIG. 10.

As shown in FIG. 3(A), the existing treatment system includes a preaccelerator 15a, a circular accelerator 16a, beam transport systems 2a and 2b, bending magnets 9a and 9b, and treatment rooms A and B. The charged particle beam accelerated to have desired energy by the circular accelerator 16a is transported to a beam irradiation device 3a in the desired treatment room A or a beam irradiation device 3b provided in the desired treatment room B by switching over the bending magnets 9a and 9b to be turned on or off for use in treatment.

First, as shown in FIG. 3(B), during a suspension period other than a treatment period, a new treatment room C and a beam irradiation device 3c (including installation such as a couch, a gantry, a beam monitor, and a scanning electromagnet) involved in the new treatment room C are installed (S101, S102), a beam transport system 2c branched off at a new bending magnet 9c and guiding the beam to the new treatment room C is provided (S103), and the new bending magnet 9c is installed in the beam transport system 2 (S104). The new bending magnet 9c is a magnet that can switch over a course for guiding the beam in accordance with an excited state. At this time, the bending magnet 9c is installed in a linear section of the beam transport system 2 of the existing system. It is thereby possible to use the beam transport system of the existing system as it is without making much adjustment even during an update work period and for a treatment facility to be continuously in service. The bending magnet 9c has an operating state of not influencing the beam passing through the beam transport system. For example, if the bending magnet 9c is turned off, it is possible to hardly influence properties of the beam passing therethrough before and after the bending magnet 9c is installed.

As the suspension period other than the treatment period for installing the equipment, nighttime hours when no treatment is given, normal holidays for the treatment facility, and a short special holiday period set for extension work, for example, can be set.

The update work period is, for example, a period since installation of new equipment for the update starts until update work is completed and the treatment system can be operated using the new devices.

The new treatment room can be installed by newly providing a shield wall or a room prepared around the existing treatment system can be used as the new treatment room.

Next, a new control system 4b is installed for controlling updated installation 20 related to this bending magnet 9c, the beam irradiation device 3c provided in the treatment room C, and the like (S105), and wire-connection between the new control system 4b and the updated installation 20 is completed (S106). In the present embodiment, the new control system 4b is regarded as an updated control system as an alternative to the existing control system 4a in the future. Nevertheless, the control system used when the treatment is continuously conducted during the update work period is preferably the existing control system 4a for which stable operation with existing installation 19 is already checked. When the updated installation 20 is tested, it is required to exercise control while combining the updated installation 20 and a part of the existing installation 19 that includes the accelerators, the transport system, and the like using the control system 4b. Owing to this, in the light of switchover of wire-connection between the existing installation 19 and the updated installation 20, it is necessary to exercise control using the existing control system 4a during the treatment period and control in a combination of the existing installation 19 with the updated installation 20 using the new control system 4b in periods other than the treatment period. Therefore, the existing installation 19 is switchably wire-connected to the control system 4a and the control system 4b (S107).

Since the work (S101 to S106) does not change the existing installation 19, a part of the work can be conducted even during the treatment period if the operation of the existing installation 19 can be used without hindrance. Furthermore, the wire-connection in (S107) is intended only to switchably enable a state of connecting the existing control system to the existing installation 19. Therefore, if each work (S101 to S107) is conducted during the period other than the treatment period, treatment can be continued using the existing installation 19 without greatly influencing a treatment schedule.

Figure 8B:
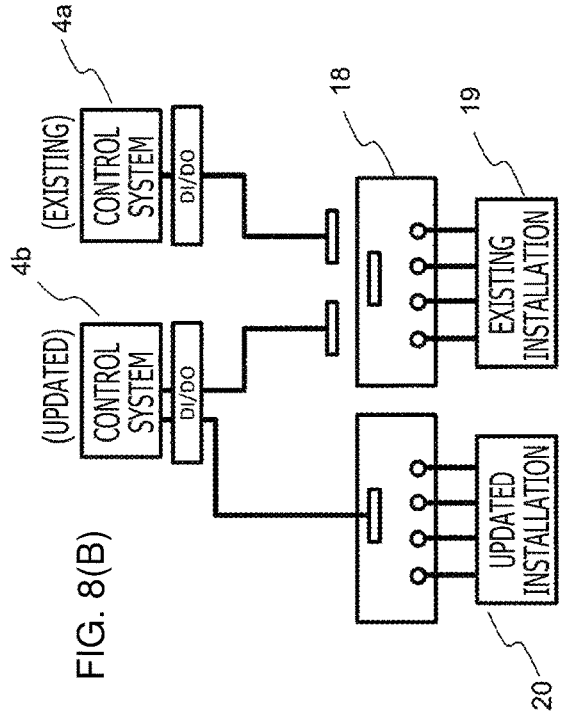
FIGS. 8(A) to 8(D) are explanatory diagrams of an update procedure related to control system in the treatment system.
Figure 8A:
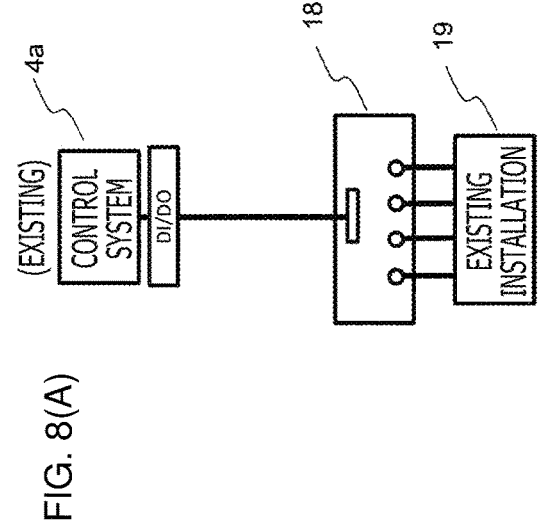
Figure 8D:
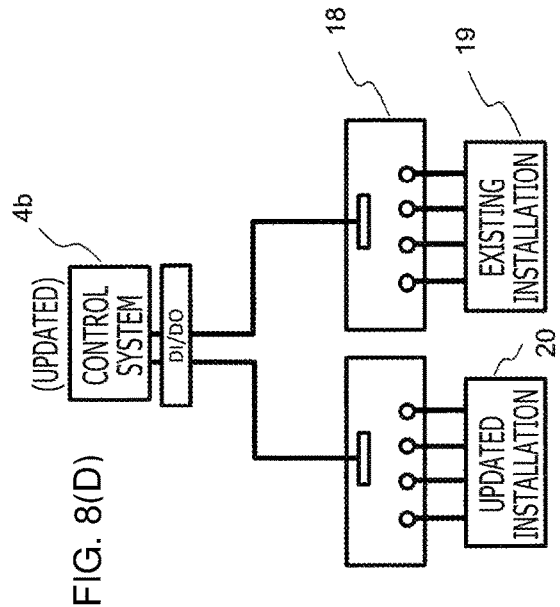

As shown in FIG. 8(A), it is assumed that wiring from an installation side is integrated into a connector terminal block 18 between the existing installation 19 and the control system 4a of the existing system, and that the existing installation 19 is connected to the control system 4a by connector-cable connection. As shown in FIG. 8(B), the wire-connection between the control system 4b and the updated installation 20 is already completed. When the updated installation 20 is subjected to beam adjustment and the like using the updated control system 4b in the periods other than the treatment period (S111), a cable-connection destination of the existing installation 19 is changed from the existing control system 4a to the updated control system 4b to thereby switch the existing installation 19 to the updated installation 20 (S110). When treatment is conducted using the existing system (S109), the cable-connection destination of the existing installation 19 is changed from the updated control system 4b to the existing control system 4a (S108). When all the update related to the control system is over, wiring from the existing installation 19 and the new installation 20 is such that the treatment system can be operated only by connection of the control system 4b to the existing installation 19 and the new installation 20 as shown in FIG. 8(D), so that the control system 4a may be removed (S206).

Figure 9A:
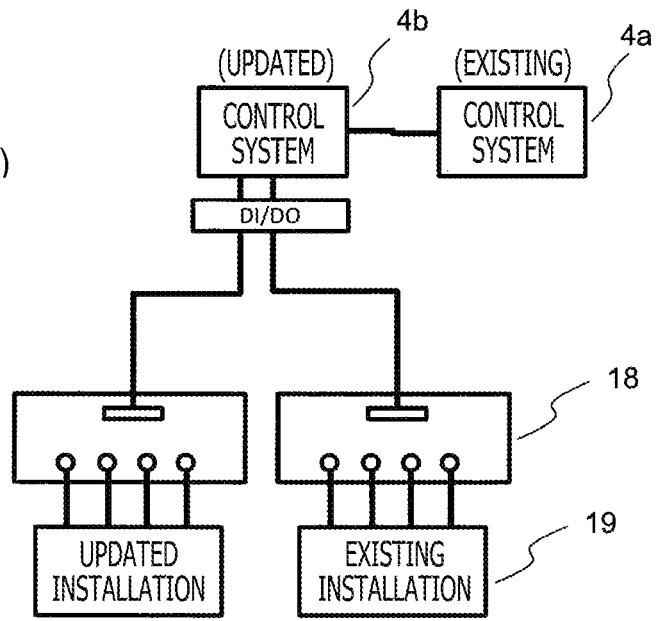
FIGS. 9(A) and 9(B) are supplementary and explanatory diagrams 1 of the update procedure related to the control system in the treatment system.
Figure 9B:
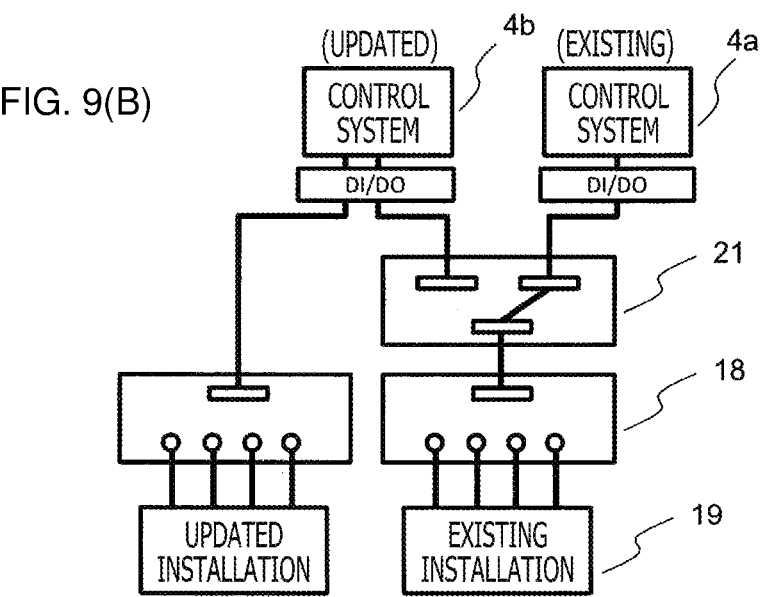
Figure 11:
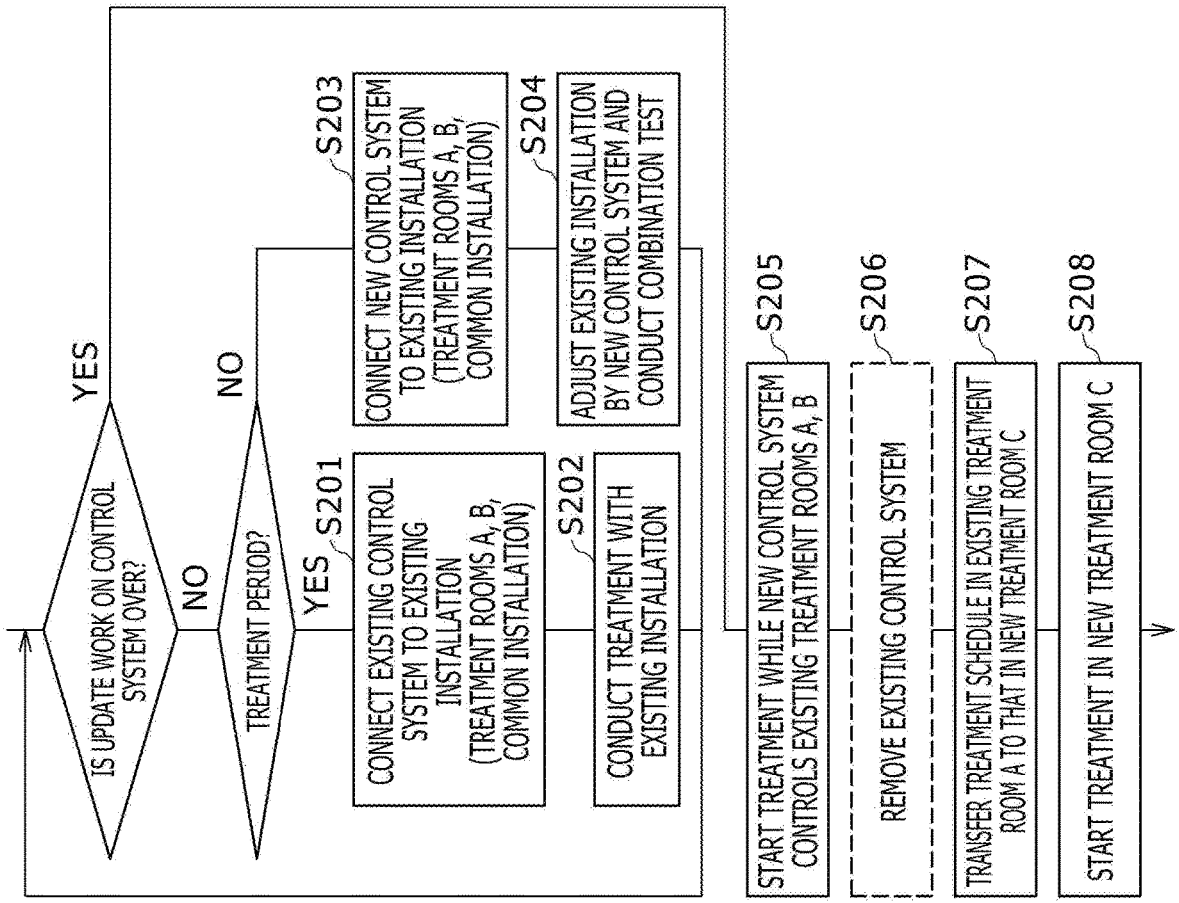
FIG. 11 is an explanatory flowchart 2 of the update procedure related to the control system in the treatment system.

As for switchover between the existing control system 4a and the updated control system 4b by change of cable connection shown in FIG. 8(B), the switchover can be made via a switch 21 such as a terminal block or an isolator having a switching function as shown in FIG. 9(B).

Figure 8C:
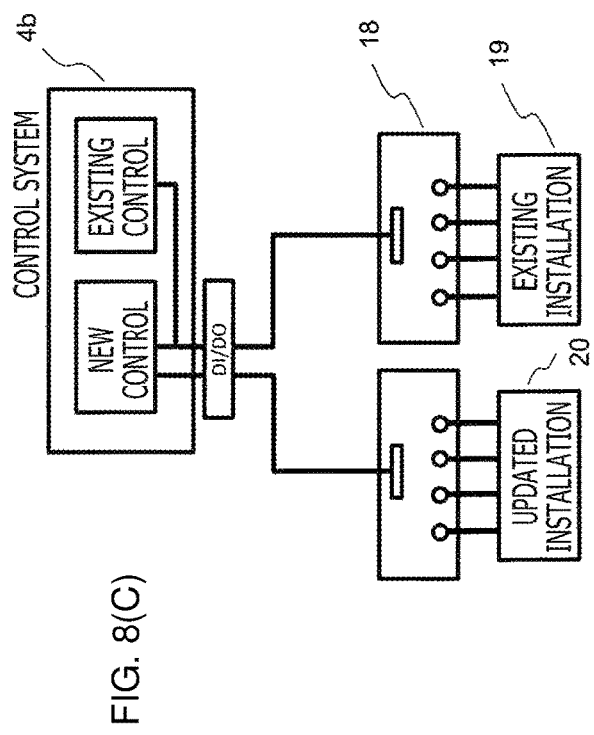

As shown in FIG. 8(C), the existing control system and the new control system can be provided integrally. In that case, instead of (S105 to S107), the new control system 4b that includes a new control section controlling the updated installation 20 and an existing control section controlling the existing installation 19 is installed, and each system is connected to the installation in such a manner as to be able to switch over between a mode for adjustment and testing with the updated installation 20 and a mode for conducting treatment with the existing installation 19.

Moreover, as for the connection change between the existing control system 4a and the updated control system 4b in relation to signals from the existing installation 19, the connection change may be realized in such a manner that the control system 4b feeds only the signals used in the existing control system 4a to the control system 4a as shown in FIG. 9(A). In that case, instead of (S106 to S107), the existing installation 19 is first disconnected from the existing control system 4a, both the updated installation 20 and the existing installation 19 are connected to the new control system 4b, and the existing control system 4a is connected to the new control system 4b so that the necessary signals can be transmitted to the existing control system 4a. A mode for controlling the existing installation 20 and conducting treatment using the existing control system 4b, and a mode for testing the existing installation 19 using the new control system 4a are provided in a switchable manner.

As shown in FIG. 3(B), during the treatment period (such as at daytime on weekdays), treatment to patients is proceeded with the beam irradiation device 3a provided in the treatment room A and with the beam irradiation device 3b provided in the treatment room B using the control system 4a while the bending magnet 9c is fixedly turned off (S109). During the periods (such as nighttime hours or holidays) other than the treatment period, a combination test with the beam irradiation device 3c provided in the treatment room C, beam adjustment, and the like are conducted using the control system 4b while the bending magnet 9c is turned on as appropriate (S111).

The procedure has been described so far for installing the updated installation related to the new treatment room C (S101 to S104), installing the new control system (S105), and conducting the adjustment and the combination test for controlling the installation related to the added treatment room C (S111) using the new control system 4b. A procedure for updating the installation in the existing treatment rooms will next be described with reference to FIGS. 3(A) to 3(F), 11 and 12.

When the beam irradiation device 3c provided in the treatment room C is completed with the adjustment to such an extent that the beam irradiation device 3c becomes available for treatment, then functions of the existing control system 4a are added to the updated control system 4b or the functions of the existing control system 4a incorporated into the new control system 4b in advance are turned on, and a test is conducted such that it is possible to control the beam irradiation device 3a provided in the existing treatment room A and the beam irradiation device 3b provided in the existing treatment room B using only the control system 4b (S204). At this time, similarly to the aforementioned, control system switchover is used either on a hardware basis by means of the switch or on a software basis by mode switchover (S201, S203), treatment is conducted using the control system 4a during the treatment period (S202), and a control function check test is conducted using the control system 4b during the periods other than the treatment period (S204).

When treatment becomes possible with the beam irradiation device 3a in the treatment room A and with the beam irradiation device 3b in the treatment room B using the control system 4b, the treatment is started using the updated control system 4b (S205) as shown in FIG. 3(C). Before start of the treatment in the treatment room C (S208), the treatment schedule with the beam irradiation device 3b in the existing treatment room B may be transferred to that for treatment with the beam irradiation device 3c in the treatment room C (S204). It is thereby possible to facilitate schedule adjustment involved in the installation update without delay. The existing control system 4a that becomes unnecessary may be removed (S206).

Subsequently, update work of the installation (such as replacement, addition, removal, and change of the control system) related to the beam irradiation device 3b in the treatment room B is conducted (S301). When the update of the installation involves the update of the control system, then it is unnecessary to switch the control system on the hardware basis since all the necessary functions out of those of the existing control system 4a are already transferred into the control system 4b or the functions are already switched over to functions prepared in the control system 4b in advance. During the treatment period, treatment is conducted with the beam irradiation device 3a in the treatment room A and with the beam irradiation device 3c in the treatment room C (S302), and the updated installation related to the beam irradiation device 3b in the newly installed treatment room B is adjusted and tested during the periods other than the treatment period (S303). At that time, the bending magnet 9b connected to the treatment room B in the process of the update work is controlled in such a manner as to be always turned off during the treatment period. Preferably, the bending magnet 9b is locked. By doing so, there is no possibility of guiding the beam used during the treatment into the treatment room in the process of the update work without installing a neutron shutter or the like. Therefore, it is possible to ensure work safety and conduct equipment installation and the like in a closed environment in the treatment room in the process of the update work.

Transferring the treatment schedule is realized by, for example, changing the treatment room B in which patients are scheduled to be treated to the treatment room C. Alternatively, transferring the treatment schedule can be realized by making a schedule such that patients who would have been scheduled to be treated in the treatment room B without the installation update are scheduled to be able to be treated in the treatment room C.

When the beam irradiation device 3b in the treatment room B after update is completed to such an extent that the beam irradiation device 3b becomes available for treatment, treatment to patients who were treated with the beam irradiation device 3a in the existing treatment room A are transferred to the treatment with the beam irradiation device 3b in the treatment room B (S304), treatment in the treatment room B is started (S305), and update work is conducted on the installation related to the beam irradiation device 3a in the treatment room A (S401). During the treatment period, treatment is conducted with the beam irradiation device 3b in the treatment room B and with the beam irradiation device 3c in the treatment room C (S402), and the adjustment and a test related to the beam irradiation device 3a in the treatment room A are conducted in the periods other than the treatment time (S403).

When the beam irradiation device 3a in the treatment room A after update is completed to such an extent that the beam irradiation device 3a becomes available for treatment, the new treatment room has been added and the installation related to the control system and the treatment room beam irradiation devices have been able to be updated for the existing treatment rooms without influencing the existing treatment rooms as shown in FIG. 3(E). If the treatment schedule in the treatment room C is transferred to that in the updated treatment room A (S404) and treatment is started (S405), then patients who were treated in the existing treatment rooms A and B are treated in the updated treatment rooms A and B, it is possible to complete the update without influence on the number of patients to be treated. Needless to say, a new patient may be additionally treated in the updated treatment room A and treatment may be started in the treatment room A (S405), while the treatment schedule in the treatment room C remains unchanged. If the treatment room C is not additionally installed but only the installation in the existing treatment rooms is updated and used with the same configuration as that of the existing configuration for a reason such as difficulty to secure a space for maintaining the new treatment room C or difficulty to maintain the number of patients, then the installation related to the beam irradiation device 3c in the treatment room C is dealt with as a makeshift treatment room for maintaining the number of patients to be treated (S406) and may be removed (S407) after end of update of the installation in the existing treatment rooms as shown in FIG. 3(F).

Figure 4A:
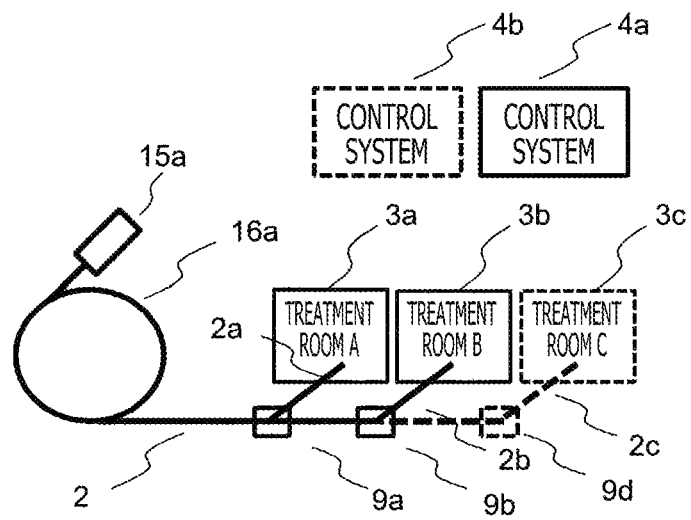
FIGS. 4(A) and 4(B) are supplementary and explanatory diagrams of the update procedure related to the treatment rooms in the treatment system.

As for addition of the beam irradiation device 3c provided in the treatment room C shown in FIG. 3(B), the bending magnet is preferably installed halfway along the transport system at which another transport system is branched off. However, as shown in FIG. 4(A), even if a branch is provided in a portion of the existing bending magnet 9b present at a terminal end of the transport system 2 and a beam transport system is extended linearly, the beam can be guided to the beam irradiation device 3c provided in the new treatment room C only when the existing bending magnets are turned off. Therefore, it is possible to add the treatment room without influence on the existing system.

Figure 4B:
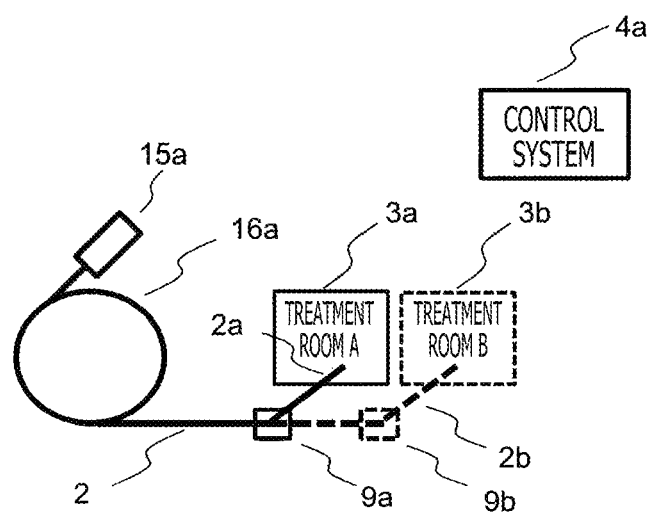

Furthermore, if it is difficult to add the treatment room, the treatment rooms may be updated one by one (the existing and updated systems are switchably used) as shown in FIG. 4(B), whereby it is possible to update the system while treatment is continued despite a reduction in the number of patients to be treated. In that case, treatment is suspended in the existing treatment room B and treatment is continued in the treatment room A during the treatment period. Updated installation is introduced into the treatment room B at other time, a new control system (not shown) is provided for controlling the updated installation, the updated installation and the control system are tested in the periods other than the treatment period. Upon completion of update of the treatment room B, the schedule in the treatment room A is transferred to that in the treatment room B, and the installation in the treatment room A is updated and tested along the flow already described above.

While the circular accelerator is used in the present embodiment, a linear accelerator can be used for implementation.

Second Embodiment

Figure 5A:
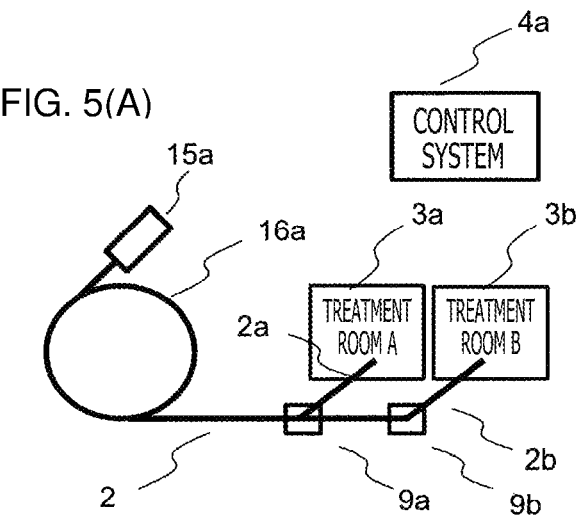
FIGS. 5(A) to 5(D) are explanatory diagrams of an update procedure related to accelerators in the treatment system.

In the present embodiment, as shown in FIG. 5(A), a treatment system that includes one circular accelerator and two treatment rooms is assumed as an existing treatment, and a procedure described below is executed in respect to update of installation related to the accelerators and the control system. It is noted that the treatment system will be described as a typical example since the number of treatment rooms, arrangement, and the like vary with installation.

Figure 5B:
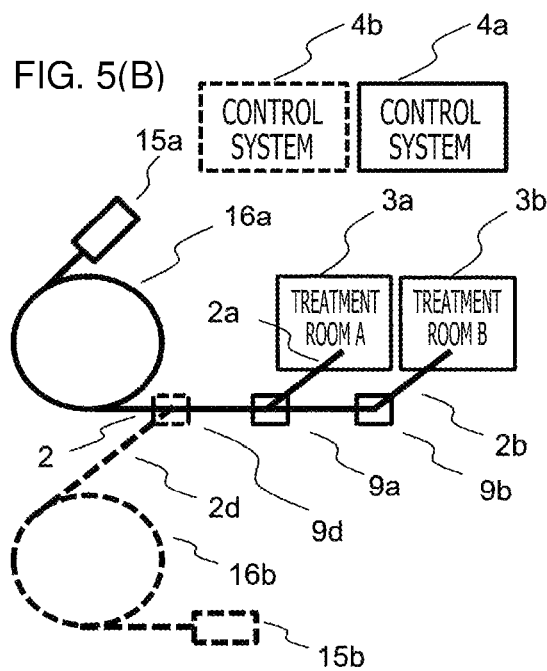

In respect to an example of the existing system of FIG. 5(A), a new preaccelerator 15b, a new circular accelerator 16b, and a new bending magnet 9d are installed, a branch is provided in the existing beam transport system 2, and a beam transport system 2d that connects the circular accelerator 16b to the branch portion of the beam transport system 2 so that the beam can be transported into the existing treatment rooms as shown in FIG. 5(B). At this time, the bending magnet 9d is installed in a linear section of the existing beam transport system 2, whereby the beam transport system 2d can be installed without influence by turning off the new preaccelerator 15b, the new circular accelerator 16b, and the new bending magnet 9d when the existing beam transport system 2 is used.

Next, the updated control system 4b is installed for controlling installation related to the preaccelerator 15b, the circular accelerator 16b, and the bending magnet 9d that are newly added, and wire-connection between the updated control system 4b and the updated installation 20 is completed. The control system 4b is regarded as the updated control system in the future. Switchover of wire-connection between the existing installation 19 and the updated installation 20 is necessary, and it is necessary to exercise control using the existing control system 4a during the treatment period and control in a combination of the existing installation 19 with the updated installation 20 using the updated control system 4b in the periods other than the treatment period. Similarly to the first embodiment, therefore, the existing installation 19 is switchably wire-connected to the control system 4a and the control system 4b, and treatment and update work are conducted.

Figure 5C:
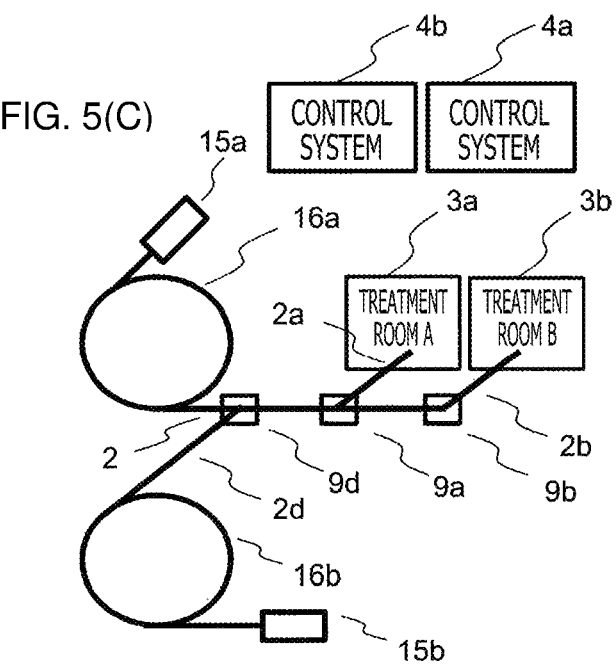

When update is completed to such an extent that treatment can be conducted with the beam irradiation device 3a in the existing treatment room A and with the beam irradiation device 3b in the treatment room B using the control system 4b, the preaccelerator 15b, the circular accelerator 16b, and the bending magnet 9d, the installation related to the accelerators has been able to be updated without influencing the existing treatment rooms as shown in FIG. 5(C).

Figure 5D:
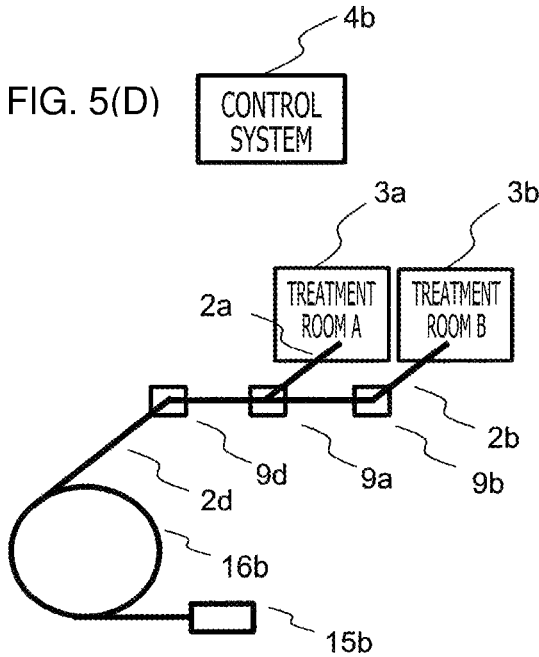

Both the existing accelerators and the updated accelerators are available by switchover of the control system. However, since the installation related to the existing control system 4a, the preaccelerator 15a, and the circular accelerator 16a becomes unnecessary, the installation may be removed as shown in FIG. 5(D).

Figure 6:
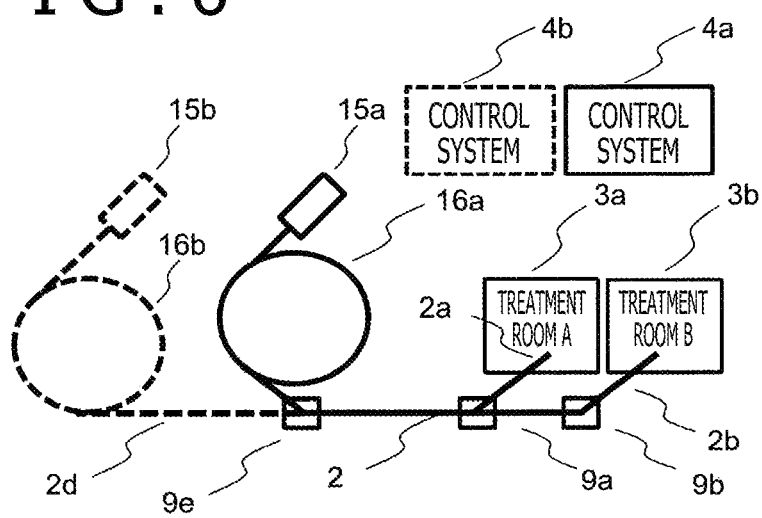
FIG. 6 is a supplementary and explanatory diagram 1 of the update procedure related to the accelerators in the treatment system.

In regard to addition of the accelerators shown in FIG. 5(B), even if a branch is provided in a portion of an existing bending magnet 9e and the beam transport system 2d is linearly connected to the accelerator, as shown in FIG. 6, the beam can be guided to the beam irradiation device provided in the existing treatment room A and B when the existing bending magnet 9e is turned off. Therefore, it is possible to add the accelerators without influence on the existing system.

Figure 7:
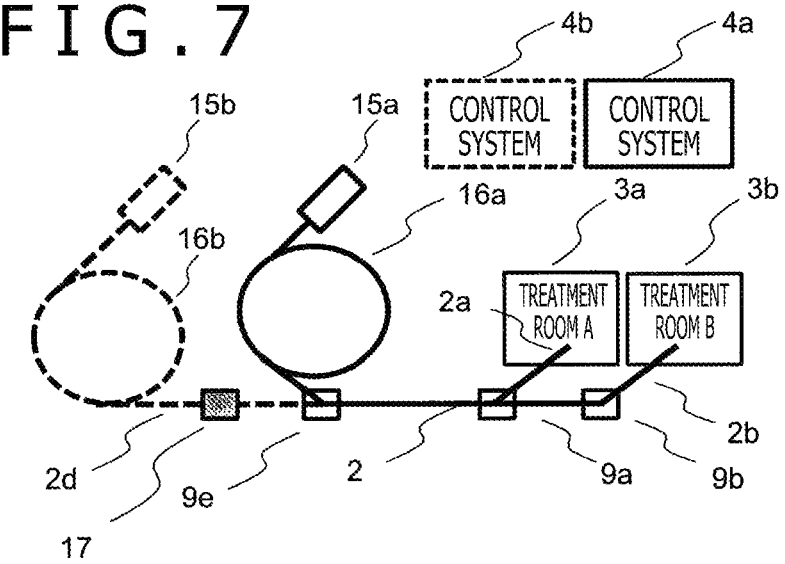
FIG. 7 is a supplementary and explanatory diagram 2 of the update procedure related to the accelerators in the treatment system.

Furthermore, as shown in FIG. 7, if the added accelerators are separated from the existing beam transport system by, for example, installing a shield (such as a neutron shutter 17), the added accelerators can be solely adjusted and tested during treatment in the existing system, thereby contributing to shortening a period required for the update.

In the first embodiment, one new treatment room is provided in such a manner as not to influence the existing system, the adjustment and the test are conducted in the periods other than the treatment time of the existing system while maintaining the number of patients to be treated per time, treatment to patients in the existing treatment rooms is transferred to treatment in the new treatment room after the treatment in the new treatment room is started, one of the treatment rooms of the existing system is made unusable, and the existing installation related to the treatment room and the control system are updated in a state of maintaining the number of patients to be treated.

In the second embodiment, one set of new accelerator installation is added for eliminating an influence on the number of patients to be treated using the existing system, adjustment of the new accelerators and the existing beam transport system and the combination test with the treatment rooms are conducted in the periods other than the treatment time of the existing system, and replacement of the existing accelerators: update is completed at timing at which treatment with the new accelerators becomes possible.

As for the update of the control system, determination as to whether to use the existing control system or to use the new control system is dealt with by simply switching over between the two control systems in a manner of disconnection depending on the cable-connection destination after integration of the wiring from the existing system into the connector terminal block in accordance with an updated portion.

By dividing the update of the installation such as the treatment rooms and the accelerators and the control system into phases and gradually implementing the update, the installing, the adjustment, and the test are conducted on the updated system in the periods (for example, during nighttime hours or on holidays) other than the treatment period and treatment is conducted as before using the existing system or the system completed with update during the treatment period (such as at daytime on weekdays). Therefore, it is possible to update the system to the new system while the particle beam treatment is continuously conducted without influence on the treatment to patients conducted before.

An advantage that can minimize the influence on the existing system is that the new bending magnet is installed in the linear section of the beam transport system of the existing system, the new beam transport system is installed in such a manner that the new beam transport system can be used only when this new electromagnet is actuated, and the new treatment room is provided at an end of the new beam transport system. If a new beam transport system and a new treatment room are provided in a linear direction with respect to the bending magnet parts at which the beam of the existing system is deflected, then the beam can be guided to the treatment rooms of the existing system when the electromagnets are actuated and the beam can be guided to the new treatment room when the electromagnets are not actuated. Therefore, the influence on the number of patients to be treated in the existing system is similarly eliminated.

According to the first embodiment, the new bending magnet is installed in the linear section of the beam transport system of the existing system, the new beam transport system capable of changing a route only when this electromagnet is actuated is installed, and the new treatment room is provided on the end of the new transport system, whereby it is possible to add the treatment room with a minimum influence on the existing system. Furthermore, if the added treatment room can be used for treatment by conducting the combination test and the adjustment using the new control system in the periods other than the treatment period of the existing system and patients in the existing treatment rooms are transferred to the new treatment room to be treated therein, it is possible to suspend or update the existing treatment rooms in a state of maintaining the number of patients to be treated as before.

It is possible to update the treatment system in a state in which the particle beam treatment is maintained in the existing system by providing an update method capable of conducting update work (additional installation, adjustment, and testing of the new system) during periods such as nighttime hours or holidays when no treatment is given in the state in which the treatment is maintained in the existing system.

Moreover, by installing the bending magnet in the linear section of the existing beam transport system and providing the new installation in such a manner as to be branched off from the linear section, there is no risk of dose exposure due to the guiding of the radiation beam during treatment and it is possible to ensure that partial update work such as installing equipment in the updated/newly provided treatment room can be conducted safely without providing the neutron shutter or the like between the existing installation and the new installation.

DESCRIPTION OF REFERENCE CHARACTERS

1: Charged particle beam generator
2: Beam transport system
2a: Beam transport system for treatment room A
2b: Beam transport system for treatment room B
2c: Beam transport system for treatment room C
2d: Beam transport system for accelerators
3: Beam irradiation device
3a: Beam irradiation device in treatment room A
3b: Beam irradiation device in treatment room B
3c: Beam irradiation device in treatment room C
4: Control system
4a: Control system (existing)
4b: Control system (updated)
5: Central control unit
6: Treatment planning device
7: Accelerator/transport system control system
8: Irradiation control system
9: Bending magnet
9a: Bending magnet (for beam transport system for treatment room A)
9b: Bending magnet (for beam transport system for treatment room B)
9c: Bending magnet (for beam transport system for treatment room C)
9d: Bending magnet (for accelerator beam transport system)
9e: Bending magnet (for accelerator beam transport system)
10: Treatment table
11: Irradiation nozzle
12: Charged particle beam
13: Patient/affected part
14: Rotating gantry
15: Preaccelerator
15a: Preaccelerator (existing)
15b: Preaccelerator (updated)
16: Circular accelerator (Synchrotron)
16a: Circular accelerator (existing)
16b: Circular accelerator (updated)
17: Neutron shutter
18: Connector terminal block
19: Existing installation
20: Updated installation
40: Operation terminal

The invention claimed is:

1. A method for updating a particle beam therapy system having an existing control system and at least one existing treatment room, comprising:
   a step of providing a new beam transport system that is added to an existing beam transport system of the particle beam therapy system at a branch off from the existing beam transport system;
   a step of providing a new treatment room that is separate from the at least one existing treatment room and that is connected to the new beam transport system;
   a step of providing a new bending magnet in the branch at which the new beam transport system is branched off from,
   wherein the branch is provided in a linear section of the existing beam transport system;
   a step of providing a new control system in addition to the existing control system;
   a step of testing a control of a first combination of the new control system with the new treatment room;
   a step of testing, after testing the first combination, a control of a second combination of the new control system with the at least one existing treatment room of the particle beam therapy system, and a step of removing, after testing the second combination, the existing control system of the particle beam therapy system.

2. The method for updating a particle beam therapy system according to claim 1, wherein the new bending magnet has an operating mode of not influencing a beam passing through the existing beam transport system.

3. The method for updating a particle beam therapy system according to claim 1, wherein the new beam transport system is provided at the branch on a most downstream side of the existing beam transport system.

4. The method for updating a particle beam therapy system according to claim 1, further comprising:

a step of integrating signal wiring from the at least one existing treatment room of the particle beam therapy system and signal wiring from the new treatment room into a connector terminal block; and a step of switching over between connection of the new control system to the signal wiring from the at least one existing treatment room and connection of the new control system to the signal wiring from the new treatment room.

5. The method for updating a particle beam therapy system according to claim 1, further comprising:

a step of integrating signal wiring from the at least one existing treatment room of the particle beam therapy system and signal wiring from the new treatment room into a switch having a switching function.

6. The method for updating a particle beam therapy system according to claim 1, wherein the testing of the first combination of the new control system with the new treatment room is performed during a period other than a treatment period in which the at least one existing treatment room of the particle beam therapy system is operated using the existing control system; and wherein the testing of the second combination of the new control system with the at least one existing treatment room is performed during the period other than the treatment period.

7. The method for updating a particle beam therapy system according to claim 6, further comprising:

a step of transferring a treatment schedule in the at least one existing treatment room to a treatment schedule in the new treatment room, before the step of testing the second combination of the new control system with the at least one existing treatment room during the period other than the treatment period.

8. A method for updating a particle beam therapy system having an existing control system and an existing accelerator, comprising:

a step of providing a new beam transport system at a branch into an existing beam transport system of the particle beam therapy system; and a step of providing a new accelerator connected to the new beam transport system, wherein the branch is provided in a linear section of the existing beam transport system.

9. The method for updating a particle beam therapy system according to claim 8, further comprising:

a step of providing a new bending magnet in the branch into the existing beam transport system.

10. The method for updating a particle beam therapy system according to claim 9, wherein the new bending magnet has an operating mode of not influencing a beam passing through the existing beam transport system.

11. The method for updating a particle beam therapy system according to claim 8, further comprising:

a step of providing a new control system;

a step of testing a control of a first combination of the new control system with the new accelerator; and a step of testing, after testing the first combination, a control of a second combination of the new control system with the existing accelerator of the particle beam therapy system.

12. The method for updating a particle beam therapy system according to claim 8, further comprising:

a step of removing, after testing the second combination, the existing control system of the particle beam therapy system.

13. The method for updating a particle beam therapy system according to claim 8, further comprising:

a step of integrating signal wiring including signal wiring from the existing accelerator of the particle beam therapy system and signal wiring from the new accelerator into a connector terminal block; and a step of switching over between connection to the signal wiring from the existing accelerator and connection to the signal wiring from the new accelerator.

14. The method for updating a particle beam therapy system according to claim 8, further comprising:

a step of integrating signal wiring from the existing accelerator of the particle beam therapy system and signal wiring from the new accelerator into a switch having a switching function.

* * * * *